(12) United States Patent
González Márquez et al.

(10) Patent No.: US 10,799,114 B2
(45) Date of Patent: Oct. 13, 2020

(54) OPEN RETINOSCOPE COUPLABLE TO A SMARTPHONE

(71) Applicants: SERVICIO ANDALUZ DE SALUD, Seville (ES); Hospital San Juan de Dios del Aljarafe, Bormujos-Sevilla (ES)

(72) Inventors: Florencio González Márquez, Bormujos-Sevilla (ES); Francisco Javier Henández Martinez, Bormujos-Sevilla (ES); Luis Gabriel Luque Romero, Seville (ES); Luis Castillón Torres, Bormujos-Sevilla (ES); Jose Luis García Garmendia, Bormujos-Sevilla (ES); Gorka Gómez Ciriza, Seville (ES); Cristina Suárez Mejías, Seville (ES); Tomás Gómez Cía, Seville (ES)

(73) Assignees: SERVICIO ANDALUZ DE SALUD [ES/ES] (ES); Hospital San Juan de Dios del Aljarafe [ES/ES] (ES)

( * ) Notice: Subject to any disclaimer, the term of this patent is extended or adjusted under 35 U.S.C. 154(b) by 0 days.

(21) Appl. No.: 15/540,735

(22) PCT Filed: Dec. 29, 2015

(86) PCT No.: PCT/ES2015/070959
§ 371 (c)(1),
(2) Date: Jun. 29, 2017

(87) PCT Pub. No.: WO2016/107953
PCT Pub. Date: Jul. 7, 2016

(65) Prior Publication Data
US 2018/0049637 A1    Feb. 22, 2018

(30) Foreign Application Priority Data
Dec. 30, 2014   (ES) .................................. 201431963

(51) Int. Cl.
| A61B 3/12 | (2006.01) |
| A61B 3/00 | (2006.01) |
| A61B 3/14 | (2006.01) |

(52) U.S. Cl.
CPC .................. *A61B 3/12* (2013.01); *A61B 3/00* (2013.01); *A61B 3/0008* (2013.01);
(Continued)

(58) Field of Classification Search
CPC ... A61B 3/0008; A61B 3/0033; A61B 3/0041; A61B 3/0075; A61B 3/14
(Continued)

(56) References Cited

U.S. PATENT DOCUMENTS

| 1,954,399 A | * | 4/1934 | Ames, Jr. ................. | A61B 3/00 269/307 |
| 5,502,520 A | * | 3/1996 | Cibis ..................... | A61B 3/113 351/200 |

(Continued)

FOREIGN PATENT DOCUMENTS

WO    2014194182 A1    12/2014

OTHER PUBLICATIONS

Internation Search Report for Application No. PCTES2015/070959 dated Mar. 8, 2016.

*Primary Examiner* — Travis S Fissel
(74) *Attorney, Agent, or Firm* — Lerner, David, Littenberg, Krumholz & Mentlik, LLP

(57) ABSTRACT

The invention relates to a novel open retinoscope comprising: a body (3) comprising a light source (31) oriented in the longitudinal direction and a first coupling means (32) for coupling to a Volk lens (51) holder in a longitudinally sliding manner; a Volk lens (51) holder (5), coupled in a longitudinally sliding manner to the body (3), where the holder (5) comprises a second longitudinal sliding coupling means (52)

(Continued)

which is complementary to the first longitudinal sliding coupling means (32) of the body (3); and a smartphone adaptor (2) which can be connected to the body (3) in a transversely sliding manner.

11 Claims, 5 Drawing Sheets

(52) U.S. Cl.
CPC .............. *A61B 3/0033* (2013.01); *A61B 3/14* (2013.01); *A61B 3/0041* (2013.01); *A61B 3/0075* (2013.01)

(58) Field of Classification Search
USPC .................................. 351/211–218, 205, 206
See application file for complete search history.

(56) References Cited

U.S. PATENT DOCUMENTS

| | | | |
|---|---|---|---|
| 5,512,966 A * | 4/1996 | Snook | A61B 3/1005 351/205 |
| 5,684,644 A * | 11/1997 | Spears | G02B 7/021 359/823 |
| 2005/0041207 A1 | 2/2005 | Miller et al. | |
| 2005/0270484 A1 | 12/2005 | Maeda et al. | |
| 2012/0320340 A1 | 12/2012 | Coleman, III | |
| 2014/0132932 A1 | 5/2014 | Jung | |
| 2014/0226061 A1* | 8/2014 | Kuehl | G02B 21/36 348/373 |
| 2014/0285766 A1* | 9/2014 | Kohn Bitran | A61B 3/14 351/206 |
| 2016/0113489 A1* | 4/2016 | Myung | A61B 3/117 351/206 |

\* cited by examiner

OPEN RETINOSCOPE COUPLABLE TO A SMARTPHONE

CROSS REFERENCE TO RELATED APPLICATIONS

The present application is a national phase entry under 35 U.S.C. § 371 of International Application No. PCT/ES2015/070959 filed Dec. 29, 2015, published as WO 2016/107953, which claims priority to Spanish Patent Application No. P201431963, filed Dec. 30, 2014, the disclosures of which are incorporated herein by reference.

OBJECT OF THE INVENTION

The present invention relates to the field of medicine, and more particularly to the field of the ophthalmology.

The object of the present invention is a novel open retinoscope for examining the fundus of the eye comprising a universal smartphone adaptor.

BACKGROUND OF THE INVENTION

Mobile telephones have been developed in recent years at a very fast pace to the point where there are now what are known as "smartphones". Not only do smartphones today have a computing capacity similar to that of computers not that many years ago, but they also feature a large number of communication devices (WiFi, Bluetooth, infrared, etc.), lighting means, means for capturing images and videos, means for playing music and videos, etc.

As a consequence of this spectacular improvement to smartphones features, a wide range of new applications have come about, among which applications in the medical field are worth mentioning. Many of the new medical applications can take advantage of the high quality of the images obtained with the digital cameras in smartphones for improving the healthcare provided to patients by their primary care physicians. They could even be used to provide healthcare to people located in isolated areas, or to simply prevent having to leave home to receive medical care. It would not be altogether unusual in a not so far-off future for even patients themselves to acquire images or videos showing their condition and send them to a medical or control center where specific protocols created for such purpose forward them to their primary care physician, who can see them and decide whether or not a visit to the consultation room is necessary, or even give a diagnosis remotely. Another important use of smartphones relates to teaching in the field of health, since they allow sharing images with students or colleagues in the profession.

This technological potential is also reaching the field of ophthalmology, where the value of images is particularly relevant, and where smartphones, with their built-in photographic and video cameras, are starting to be used as examination tools.

Examination of the fundus of the eye in most medical consults today is based on using and operating a conventional direct ophthalmoscope. However, conventional direct ophthalmoscopes have a series of drawbacks that limit their use, such as the fact that the examined visual field is too small to assess the peripheral retina, for example. Furthermore, with this device it is not possible to obtain graphic images that can later be assessed or shared.

There are more sophisticated ophthalmoscopes with better features on the market, such as the PanOptic ophthalmoscope, for example. The PanOptic ophthalmoscope allows seeing a larger retinal field, and by using a specific iPhone adaptor (iExaminer, manufactured by Wellch Allyn), it can obtain images and videos of the fundus of the eye. However, only a specific version of this smartphone can be coupled to the PanOptic ophthalmoscope. Furthermore, it is a complex and expensive device and when used without the pupil being dilated, its visual field is not very large either.

A contactless specific adaptor between smartphones and ophthalmological lenses (EyeGo adaptor) which allows coupling a specific smartphone to a given ophthalmological lens is also known. However, these adaptors require light from the modulated smartphone in order to examine the eye. Furthermore, not just any smartphone can be used, since said smartphone must have a specific light source for said examination which is activated by means of a specific app. Therefore, this adaptor cannot be used as an independent examining tool without the aid of a specific smartphone coupled specifically to the adaptor and having specific functions and features.

DESCRIPTION OF THE INVENTION

The object of the present invention is a novel open retinoscope designed for examining the fundus of the eye which associates a light source with an ophthalmological Volk lens, allowing the physician to assess the retina of a patient in a simpler manner and with a much larger visual field than with any direct ophthalmoscope available today. The open retinoscope of the invention includes a smartphone adaptor which allows the coupling of a smartphone to collect the images obtained during the examination. Furthermore, unlike other devices available today, the smartphone adaptor of the retinoscope of the invention allows coupling any smartphone model on the market. This novel retinoscope is portable, cost-effective and easy to handle. Furthermore, since it has its own light source, it allows examining the fundus of the eye independently, i.e., without requiring coupling to a smartphone.

The open retinoscope of the invention comprises in one embodiment a body, a Volk lens holder, and a smartphone adaptor. Each of these elements is described below in greater detail.

a) Body

The body is the central element of this device on which most of the other elements are fixed. The body essentially comprises a light source oriented in the longitudinal direction and a first coupling means for coupling, in a longitudinally sliding manner, to a Volk lens.

The light source, preferably an LED, is responsible for lighting up the eye of the patient during the examination. Preferably, a mechanical system allows vertically moving a lighting system as needed for the examination, for the purpose of focusing light directly on the center of the Volk lens, and where appropriate, being adapted to the needs of the connected smartphone. According to another preferred embodiment of the invention, the body further comprises a housing for power cells which provide energy to the light source. The body of the invention can also comprise a switch for switching on the light source.

As regards the orientation, as discussed above the light source is oriented in the longitudinal direction. In this context, the "longitudinal" direction must be understood as the direction going from the position where the objective of the camera of a smartphone coupled to the adaptor is located to the center of the Volk lens. In other words, it is the natural direction of orientation of the open retinoscope when it is used for examining the eye of a patient, either with or without a smartphone coupled thereto.

In turn, the coupling means for a Volk lens is configured for receiving a Volk lens that will be aligned with the camera of the smartphone coupled to the adaptor according to the longitudinal direction, wherein the distance between the camera of the smartphone and the Volk lens can be modified, as will be seen below.

In principle, the body can have any shape provided that it can carry out the tasks described above. However, in a preferred embodiment of the invention the body is formed by a longitudinal portion incorporating the first coupling means, and a transverse portion incorporating a fourth coupling means and the light source. Both portions are rigidly connected such that they form a single piece.

b) Volk Lens Holder

This holder is coupled, in a longitudinally sliding manner, to the body for moving the Volk lens closer to or away from the objective of the camera of the smartphone as needed for the examination procedure. To that end, the holder comprises a second longitudinal sliding coupling means which is complementary to the first longitudinal sliding coupling means of the body. The first and second coupling means can consist of tongue and groove tracks. The holder can be configured in different ways provided that it can be coupled to the body in a sliding manner as described above. For example, in a preferred embodiment of the invention the holder is a circular or partially circular holder with elastic features that are sufficient for gripping the Volk lens in it.

c) Smartphone Adaptor

The adaptor is an adaptor which can be connected to the body in a transversely sliding manner, such that the smartphone can be fixed in the transverse position suited for the purpose of being able to align the objective of its camera with the Volk lens. In this context, the "transverse" direction is understood as a horizontal direction perpendicular to the longitudinal direction described above.

In a preferred embodiment of the invention, the adaptor comprises on a first face an adjustable fixing means for smartphones and on an opposite second face a third transverse sliding coupling means which is complementary to the fourth transverse sliding coupling means of the body.

Preferably, the adjustable fixing means for smartphones of the first face of the adaptor comprises a fixed flange and a transversely adjustable flange, such that it moves closer to and away from said fixed flange, thereby gripping the smartphone between both.

In turn, the third transverse sliding coupling means of the second face of the adaptor can be configured as a pair of tongue and groove tracks which are complementary to another pair of tracks of the body forming the fourth transverse sliding coupling means. The adaptor can thereby slide with respect to the body in order to locate the smartphone in the most suitable position depending on the model.

Sometimes it is desirable to support the retinoscope on the face of the patient to prevent unwanted movements and changes in distance or orientation with respect to the Volk lens. To that end, the invention further comprises a longitudinally projecting support element coupleable to the body in a longitudinally sliding manner. In other words, the support element projects a configurable distance with respect to the front area of the retinoscope of the invention. To change that distance, the support element preferably comprises a fifth longitudinal sliding coupling means which is complementary to a sixth longitudinal sliding coupling means of the body. Both coupling means can be configured as tongue and groove tracks.

It is also sometimes convenient to use a magnifier between the lighting means and the lens to enlarge the image obtained for the purpose of better distinguishing details. Therefore, the retinoscope of the present invention preferably further comprises a magnifier holder coupleable in a longitudinally sliding manner between the lens holder and the lighting means. To that end, the magnifier holder preferably comprises a seventh longitudinal sliding coupling means which is complementary to an eighth longitudinal sliding coupling means of the Volk lens holder.

Although the various coupling means used in the invention can preferably be implemented as complementary tongue and groove tracks as described above, it must be mentioned that in all cases each pair of coupling means could be implemented respectively as a rack and a toothed rod moving by means of a wheel, which allows achieving a more precise movement of each element in question.

The invention also relates to separately protecting each of the elements coupleable to the open retinoscope described in the preceding paragraphs.

Therefore, another aspect of the invention relates to a support element coupleable to an open retinoscope such as the one described above, wherein the support element comprises a fifth longitudinal sliding coupling means which is complementary to the sixth longitudinal sliding coupling means of the body of the open retinoscope.

Another additional aspect of the invention relates to a magnifier holder coupleable to a retinoscope such as the one described above, wherein the holder comprises a seventh longitudinal sliding coupling means which is complementary to the eighth longitudinal sliding coupling means for the Volk lens of the open retinoscope.

PREFERRED EMBODIMENT OF THE INVENTION

Figure 1A:
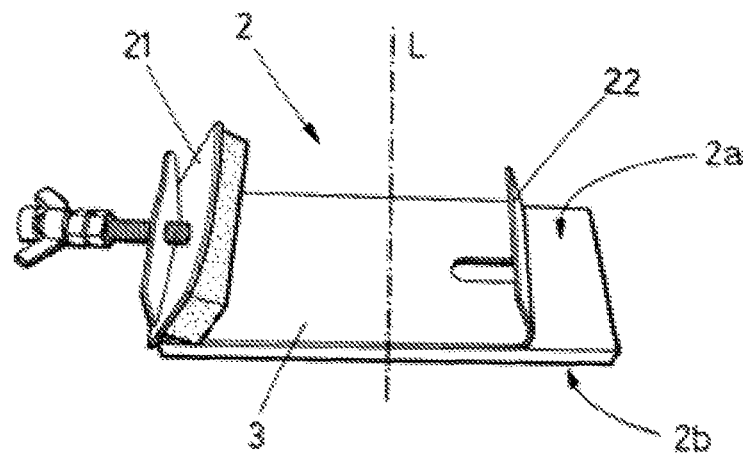
FIGS. 1a and 1b show two perspective views of an example of an adaptor according to the invention.
Figure 1B:
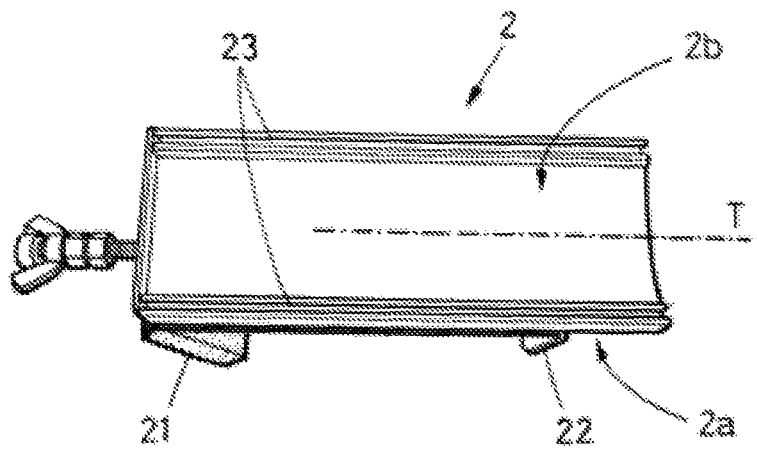

FIGS. 1a and 1b show respective views of a smartphone adaptor (2) according to the invention. The adaptor (2) is the part of the open retinoscope (1) which allows the fixing of a smartphone and is formed by a planar plate having a first face (2a) and a second face (2b).

On the first face (2a), seen in greater detail in FIG. 1a, there is located an adjustable fixing means (21, 22) for a smartphone formed by a fixed flange (22) and a moving flange (21) which can be transversely adjusted for gripping the smartphone (not shown in the drawings). The movement of the moving flange (21) is achieved by means of a screw shown on the left in the drawings.

On the second face (2b), seen in greater detail in FIG. 1b, there is located a third coupling means (23) for coupling by sliding in the transverse direction. As can be seen, this third coupling means (23) is configured as a pair of tongue and groove tracks which, as will be seen below, will be coupled to a fourth transverse coupling means (33) of the body (3).

For greater clarity, FIG. 1a depicts a line (L) corresponding to the longitudinal plane, and FIG. 1b depicts a line (T) corresponding to the transverse plane.

Figure 2A:
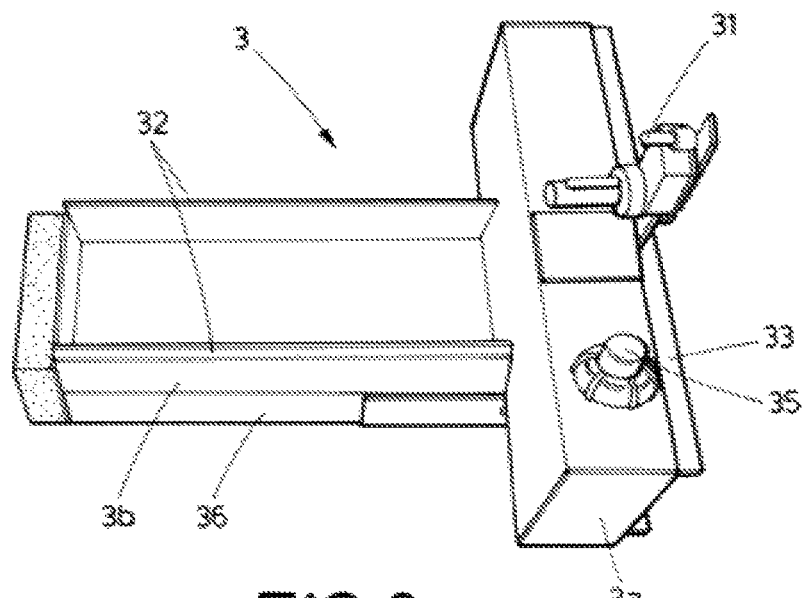
FIGS. 2a and 2b show two perspective views of an example of a body according to the invention.
Figure 2B:
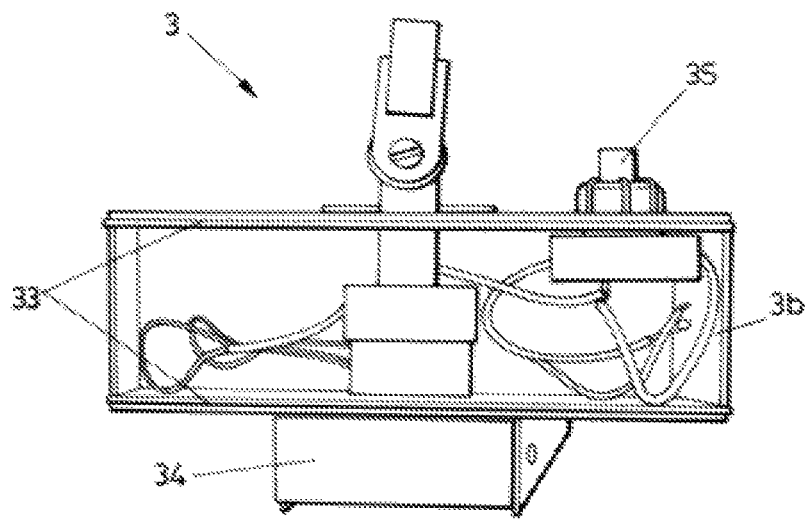

FIGS. 2a and 2b show two perspective views of the body (3) according to the invention. The body (3) is essentially formed by a transverse portion (3a) coupled to a longitudinal portion (3b).

The transverse portion (3a) has a parallelepiped shape oriented in the transverse direction on the proximal face of which (the face closest to the smartphone during use of the open retinoscope (1)) there is located the fourth transverse coupling means (33). This fourth coupling means (33) is configured as a pair of tongue and groove tracks which are complementary to the tracks of the third coupling means (23) of the adaptor (2). Therefore, the adaptor (2) can be coupled to the body (3) in a sliding manner to locate the position of the camera of the smartphone in the required position.

The transverse portion (3a) also holds a small central vertical projection where the light source (31), usually an LED, is located. There is also included a system which allows moving the light source (31) up or down so that it is facing the Volk lens (51), which will be described below, and also aligned with the objective of the camera of the smartphone. The transverse portion (3a) also has a switch (35) for switching the light source (31) on or off. The corresponding wiring housed inside the parallelepipedic volume of the transverse portion (3a), which is open on the proximal face thereof in this example, can be seen in FIG. 2b.

The longitudinal portion (3b) also has a parallelepipedic shape attached to the area of the lower edge of the transverse portion (3a) and oriented in the longitudinal direction. The longitudinal portion (3b) has a first longitudinally sliding coupling means (32) on the upper face thereof intended for the coupling of a Volk lens (51), as will be described below. This first coupling means (32) consists of a pair of tongue and groove tracks located on the upper side edges of the longitudinal portion (3b) which extend in the longitudinal direction.

The lower face of the longitudinal portion (3b) furthermore has a sixth longitudinal coupling means (36) configured as a pair of tongue and groove tracks running along the lower side edges of the longitudinal portion (3b) which extend in the longitudinal direction. This sixth coupling means (36) can be used, as will be described below, for the coupling of a support element (6) which can be used for supporting the open retinoscope (1) on the face of the patient.

The longitudinal portion (3b) also comprises a housing (34) for the power cells for the light source (31). This housing (34) is located in the most proximal part of said longitudinal portion (3b) so that the cells are close to the transverse portion (3a) housing the wiring and the light source (31) itself.

Figure 3:
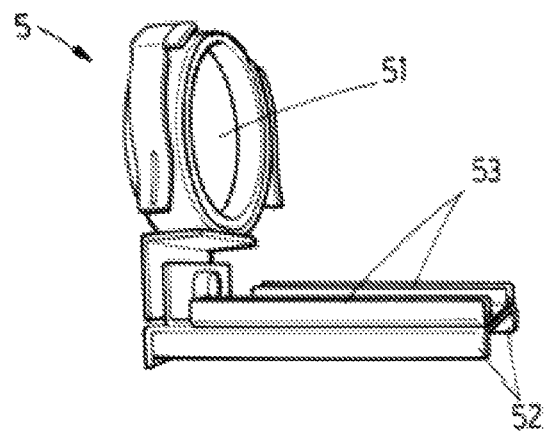
FIG. 3 shows a perspective view of an example of a Volk lens holder according to the invention.

FIG. 3 shows an example of a Volk lens (51) suitable for coupling to the longitudinal portion (3b) of the body (3) shown in the preceding figures. The Volk lens (51) is vertically mounted in a circular holder (5) arranged perpendicular to a horizontal base having a second longitudinally sliding coupling means (52) configured as a pair of downwardly oriented tongue and groove tracks. This second coupling means (52) is complementary to the first coupling means (32) of the longitudinal portion (3b) of the body (3), such that the holder (5) can be coupled to the body (3) in a sliding manner to allow moving the Volk lens (51) closer or further away.

The Volk lens holder (5) of FIG. 3 has also an eighth coupling means (53) configured as a pair of upwardly oriented tongue and groove tracks. This eighth coupling means (53) can be used for coupling a magnifier holder (7), as will be seen below.

Figure 4:
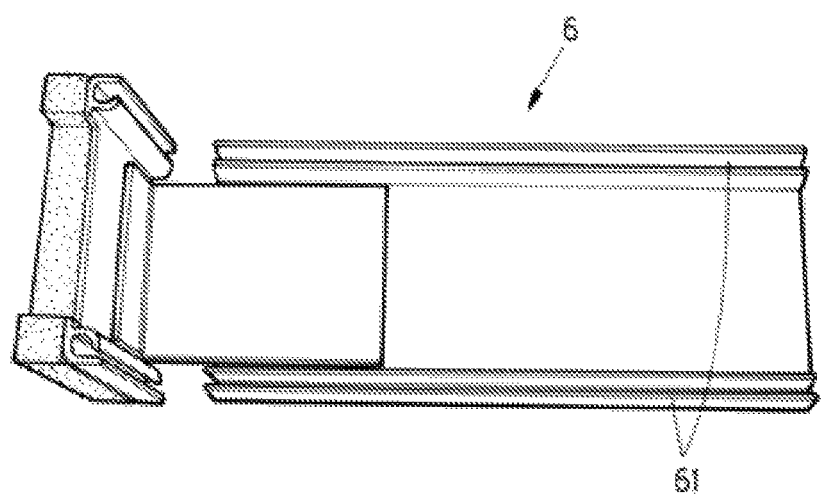
FIG. 4 shows a perspective view of an example of a support element according to the invention.

FIG. 4 shows an example of a support element (6) according to the invention. This support element (6) is essentially formed by a padded end fixed to a base provided with a fifth longitudinal coupling means (61). This fifth longitudinal coupling means (61) is configured as a pair of tongue and groove tracks which are complementary to the sixth coupling means (36) located on the lower face of the longitudinal portion (3b) of the body (3).

Figure 5A:
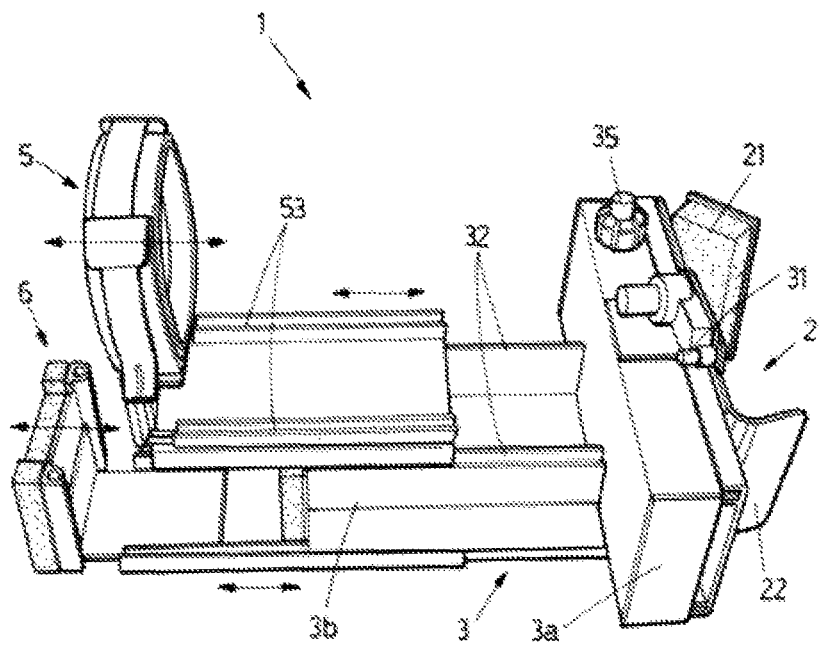
FIGS. 5a and 5b show two perspective views of an open retinoscope according to the invention further comprising a support element.
Figure 5B:
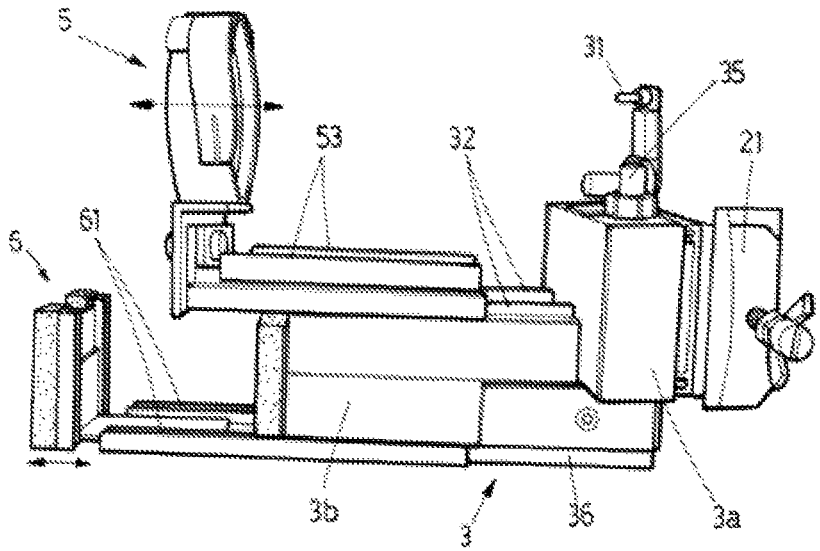

FIGS. 5a and 5b show respective perspective views showing an example of an open retinoscope (1) according to the invention provided with a support element (6). As can be seen, the Volk lens (51) holder (5) can slide longitudinally as a result of the second coupling means (52) of the holder (5) and the first coupling means (32) of the body (3) being complementary to one another. This allows moving the Volk lens (51) closer to and away from the objective of the camera of the smartphone and the light source (31), as needed. The support element (6), in turn, can also slide longitudinally as a result of the fifth coupling means (61) of said element (6) and the sixth coupling means (36) of the lower face of the longitudinal portion (3b) of the body being complementary to one another. This allows moving the padded end of the support element (6) closer and farther away to support it on the face of the patient as needed. In turn, the adaptor (2) can slide transversely as a result of the third transverse coupling means (23) of the adaptor (2) being complementary along the fourth coupling means (33) of the body (3).

Figure 6:
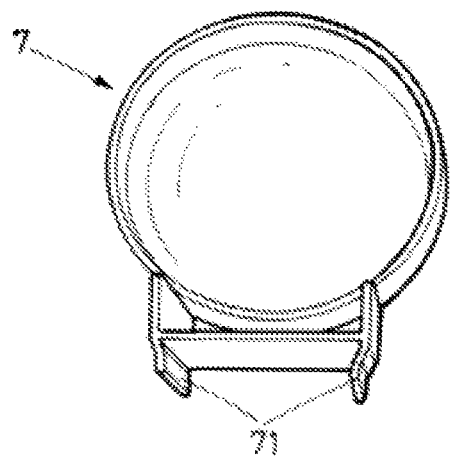
FIG. 6 shows a perspective view of a magnifier holder according to the invention.

Finally, FIG. 6 shows a magnifier holder (7) intended for being coupled to the open retinoscope (1) of the invention. This holder (7) has a seventh coupling means (71) configured as a pair of tongue and groove tracks having a short length which are complementary to the eighth coupling means (53) located on the upper face of the base of the Volk lens (51) holder (5).

Figure 7:
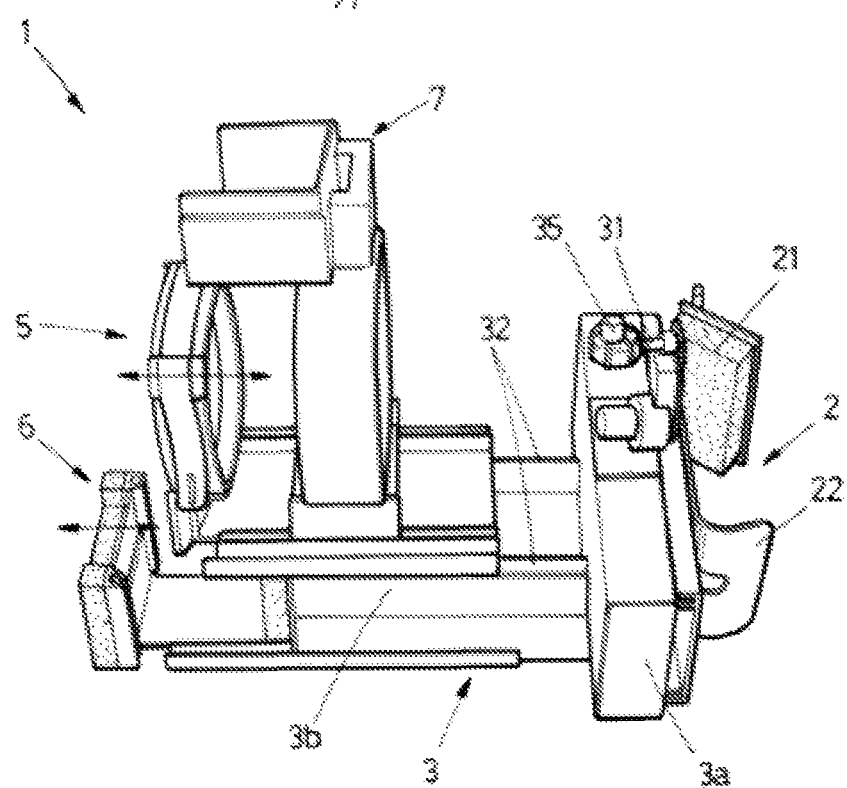
FIG. 7 shows a perspective view of an open retinoscope according to the invention further comprising a support element and a magnifier holder.

Therefore, as shown in FIG. 7, this magnifier holder (7) can be coupled to the base of the Volk lens (51) holder (5), such that the magnifier is aligned with the Volk lens (51) and with the objective of the camera of the smartphone, and can move longitudinally in order to move closer to or away from one another, as needed.

The invention claimed is:

1. An open retinoscope coupleable to a smartphone, the retinoscope comprising:
   a body comprising a traverse portion coupled to a longitudinal portion, a light source oriented in a longitudinal direction and a first longitudinal sliding coupling means,
   a Volk lens holder including a Volk lens and a second longitudinal sliding coupling means complementary to the first longitudinal sliding coupling means for coupling the Volk lens holder to the body such that the Volk lens is slidable relative to the body in the longitudinal direction, such that a first adjustable distance is established as the distance from the smartphone to the Volk lens holder;

a support element coupleable to the body and slidable relative to the body in the longitudinal direction, the support element being configured to support the retinoscope on a patient's face, the support element comprising a fifth longitudinal sliding coupling means complementary to a sixth longitudinal sliding coupling means located on the lower face of the longitudinal portion of the body such that a second adjustable distance is established as the distance from the smartphone to the patient's face; and a smartphone adaptor being connectable to the body and slidable relative to the body in a direction transverse to the longitudinal direction, wherein a height of the light source is adjustable relative to the body and independently from the smartphone, wherein the Volk lens holder and the support element are independently slidably adjustable such that the first and second distances are independently adjustable, the adjustment of the first distance not changing the second distance and the adjustment of the second distance not changing the first distance.

2. The open retinoscope according to claim 1, wherein the smartphone adaptor comprises a first face and a second face opposite the first face, the first face having an adjustable fixing means for a smartphone and the second face having a first transverse sliding coupling means complementary to a second transverse sliding coupling means of the body.

3. The open retinoscope according to claim 2, wherein the adjustable fixing means of the smartphone adaptor comprises a fixed flange and an adjustable flange such that the adjustable flange is moveable in the transverse direction relative to the fixed flange.

4. The open retinoscope according to claim 2, wherein the body comprises a longitudinal portion incorporating the first longitudinal sliding coupling means and a transverse portion incorporating the second transverse sliding coupling means and the light source.

5. The open retinoscope according to claim 1, wherein the body further comprises a housing for containing power cells for the light source.

6. The open retinoscope according to claim 1, wherein the body further comprises a switch for controlling power to the light source.

7. The open retinoscope according to claim 1, wherein the light source is an LED.

8. The open retinoscope according to claim 1, further comprising a magnifier holder coupleable to the Volk lens holder and slidable in the longitudinal direction between the Volk lens holder and the light source.

9. The open retinoscope according to claim 8, wherein the magnifier holder comprises a seventh longitudinal sliding coupling means complementary to an eight longitudinal sliding coupling means of the Volk lens holder.

10. A combination of a magnifier holder and the open retinoscope according to claim 1, wherein the magnifier holder comprises a seventh longitudinal sliding coupling means complementary to an eight longitudinal sliding coupling means of the Volk lens holder of the retinoscope.

11. An open retinoscope coupleable to a smartphone, the retinoscope comprising:

a body comprising a light source oriented in a longitudinal direction and a first longitudinal sliding coupling means, a Volk lens holder including a Volk lens and a second longitudinal sliding coupling means complementary to the first longitudinal sliding coupling means for coupling the Volk lens holder to the body such that the Volk lens is slidable relative to the body in the longitudinal direction, a support element coupleable to the body and slidable relative to the body in the longitudinal direction, the support element being configured to support the retinoscope on a patient's face, and a smartphone adaptor being connectable to the body and slidable relative to the body in a direction transverse to the longitudinal direction, a first distance being defined as the distance from the smartphone to the Volk lens holder, a second distance being defined as the distance from the smartphone to the support element, wherein the first distance and the second distance are independently adjustable such that the first distance can be adjusted without changing the second distance and the second distance can be adjusted without changing the first distance, wherein a height of the light source is adjustable relative to the body and independently from the smartphone.

* * * * *